United States Patent [19]
Tyman et al.

[11] Patent Number: 5,424,421
[45] Date of Patent: Jun. 13, 1995

[54] SYNTHESIS OF CARMINIC ACID AND PRINCIPAL INTERMEDIATES

[75] Inventors: John H. P. Tyman, Uxbridge, United Kingdom; Alberto Fiecchi, deceased, late of Milan, Italy, by Giuseppina Gandini, Alessandro Fiecchi, Giuliana Fiecchi and Donata Fiecchi, legal representatives

[73] Assignee: European Colour PLC, United Kingdom

[21] Appl. No.: 969,262

[22] PCT Filed: Jul. 15, 1991

[86] PCT No.: PCT/GB91/01170
§ 371 Date: Mar. 17, 1993
§ 102(e) Date: Mar. 17, 1993

[87] PCT Pub. No.: WO92/01664
PCT Pub. Date: Feb. 6, 1992

[30] Foreign Application Priority Data

Jul. 17, 1990 [GB] United Kingdom ............... 9015703
Feb. 28, 1991 [GB] United Kingdom ............... 9104204

[51] Int. Cl.⁶ .................... C08B 37/00; C09B 1/00
[52] U.S. Cl. ...................... 536/124; 536/1.11; 536/119; 536/120; 552/208; 552/261; 552/262; 552/268; 552/290
[58] Field of Search .......... 536/1.11, 4, 1, 18.1, 536/120, 119, 120, 124; 552/208, 261, 262, 268, 290

[56] References Cited

U.S. PATENT DOCUMENTS

| | | | |
|---|---|---|---|
| 4,826,962 | 5/1989 | Rathbone et al. | 536/122 |
| 4,855,415 | 8/1989 | Sugiyama et al. | 536/17.4 |
| 4,933,398 | 6/1990 | Fischer et al. | 525/504 |
| 5,013,852 | 5/1991 | Walenta et al. | 549/362 |
| 5,023,239 | 6/1991 | Ogura et al. | 514/26 |

OTHER PUBLICATIONS

Dimroth, O.; Kämmerer, H. *Chem. Ber.* 1920, 53(4), 471–480.
Zahn, K.; Ochwat, P. *J. Liebigs Ann. Chem.* 1928, 462, 72–97.
Wheeler, A. S.; Edwards, V. C. *J. Am. Chem. Soc.* 1917, 39, 2460–2468.
Bruce, D. B.; Thomson, R. H. *J. Chem. Soc.* 1955, 1089–1096.
Kraus, G. A.; OnMan, T. *Synth. Commun.* 1986, 16, 1037–1042.
Allevi, P. et al. *J. Chem. Soc., Chem. Commun.* 1987, 101–102.
Allevi, P. et al. *J. Chem. Soc., Chem. Commun.* 1987, 1245–1246.
Australian Journal of Chemistry, vol. 34, No. 11, 1981 (Melbourne, AU) D. W. Cameron et al; "Chemistry of the coccoidea. VIII. Synthesis of the Ancient Dyestuff Kermesic Acid and of Related Anthraquinones" pp. 2401–2421, see pp. 2407–2408.
Journal of the Chemical Society, Perkin Transactions I, 178 (Letchworth, GB) G. Roberge et al; "Total Syntheses of the methyl ester derivatives of the coccid anthraquinones laccaic acid D and Kermesic Acid", pp. 1041–1046, see the whole article.
Tetrahedron Letters, No. 18, 1968, Pergamon Press, (GB) D. D. Gadgil et al; "Structure of Kermesic Acid", pp. 2223–2227 see the whole article.
Journal of the Chemical Society, Chemical Communications, 178, (Letchworth, GB) D. W. Cameron et al; "Synthesis of the Insect Dyestuff Kermesic Acid and Related Anthroquinones":, pp. 688–689 see the whole article.

*Primary Examiner*—Douglas W. Robinson
*Assistant Examiner*—Kathleen Kahler Fonda

[57] ABSTRACT

The invention relates to the synthesis of 6-deoxykermesates, 6-deoxykermesic acid, and carminic acid, based on a reaction of a 2-halogenonapthazarin with a bis-trimethylsilyl-diene.

28 Claims, 2 Drawing Sheets a: $R_1 = OH; R_2 = H$
b: $R_1 = R_2 = H$
c: $R_1 = OAc; R_2 = Ac$
d: $R_1 = H; R_2 = Ac$

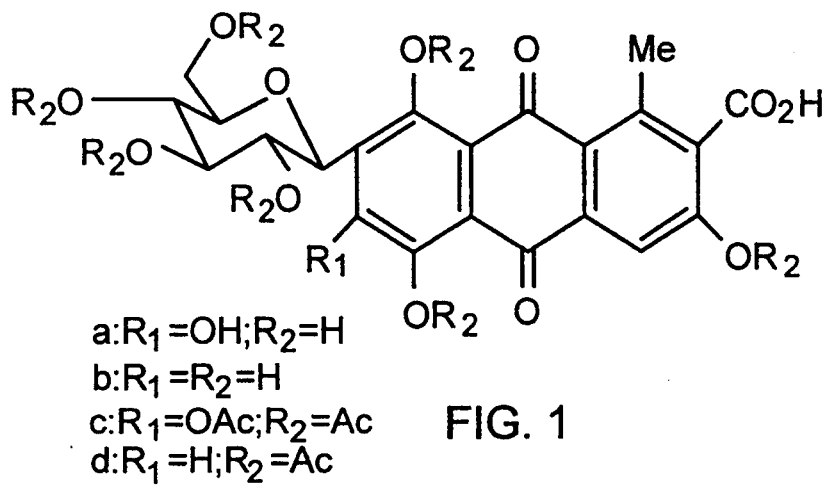
FIG. 1
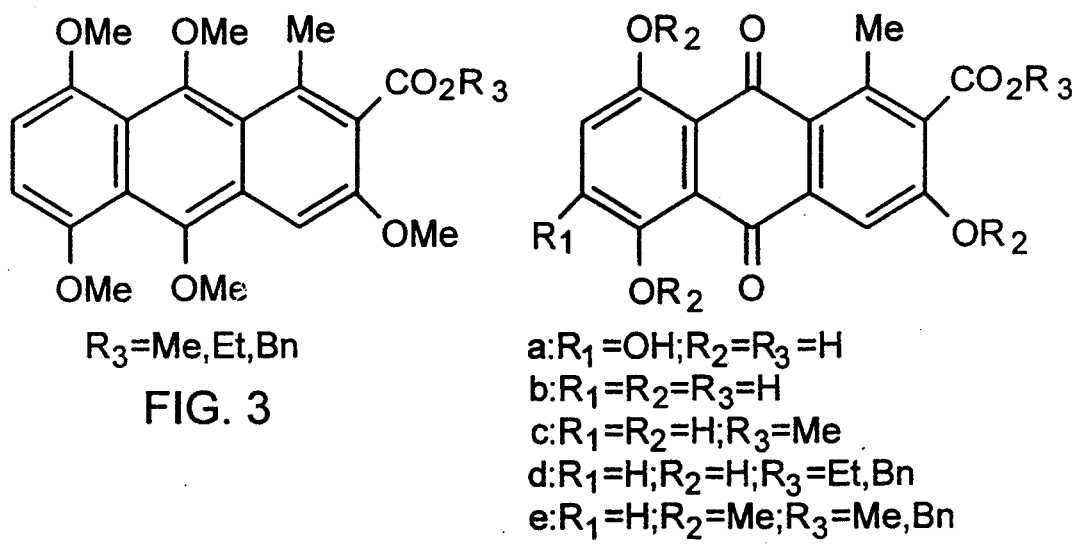
FIG. 2
FIG. 3
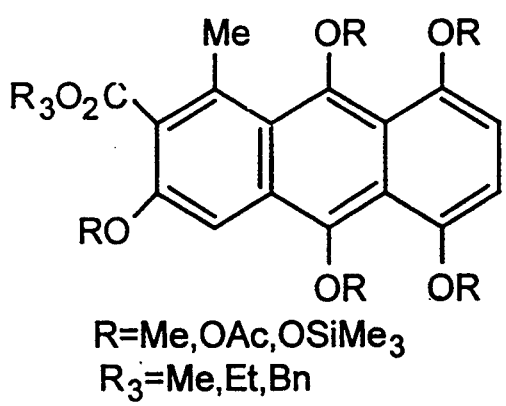
FIG. 3A $R_3$=Me,Et,Bn $R_3$=Me,Et,Bn a: $R_1$=Bn; $R_2$=Me; $R_3$=Me
b: $R_1$=H; $R_2$=Me; $R_3$=Me
c: $R_1$=$R_3$=H; $R_2$=Me
d: $R_1$=Ac; $R_2$=Me; $R_3$=H
e: $R_1$=Ac; $R_2$=$R_3$=H
f: $R_1$=$R_2$=Ac; $R_3$=H
g: $R_1$=$R_3$=Bn; $R_2$=Me

SYNTHESIS OF CARMINIC ACID AND PRINCIPAL INTERMEDIATES

This invention relates to the synthesis of carminic acid (7-β-D-glucopyranosyl-1-methyl-3,5,6,8-tetrahydroxyanthra-9,10-quinone-2-carboxylic acid) and principal intermediates; alkyl 6-deoxykermesates (alkyl 3,5,8-trihydroxy-1-methyl-9,10-anthraquinone-2-carboxylates) and 6-deoxycarminic acid.

The hydroxyanthraquinone structure is common to a number of antibiotics such as carminomycin and to the natural colouring material carminic acid

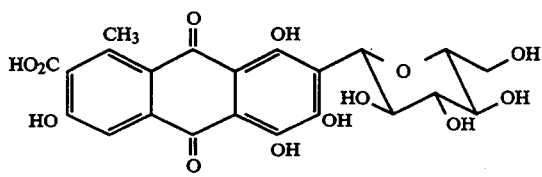

which is the 7-β-(D)glucosyl derivative of kermesic acid.

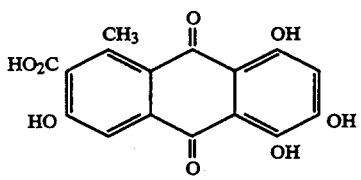

Carminic acid, the colourant principle of cochineal, is extracted from the dried female bodies of the insect species *Dactylopius coccus Costa* which feed on the wild cactus *Nopalla coccinellifera*. The natural supply is variable and subject to large price fluctuations, and therefore it is desirable to produce carminic acid by synthetic means Kermesic acid is obtained from *Kermes illicis*.

The present invention provides intermediates for the synthesis of kermesic acid and carminic acid.

The invention comprises, in one aspect, the synthesis of alkyl 6-deoxykermesates by reaction of a 2-halogenonaphthazarin (2-halogeno-5,8-dihydroxy-1,4-naphthoquinone) with a bis-trimethylsilyl-diene (bis-TMS-diene). 2-Halogenonaphthazarin dimethyl ether or diacetate may be used. Throughout the specification the term "alkyl" is to be understood to include a "benzyl" group.

The 2-halogenonanphthazarin may be 2-chloronaphthazarin.

A Friedel-Crafts reaction may be used to synthesize 2-chloronaphthazarin or chlorine may be added to naphthazarin to give the adduct, 2,3-dichloronaphthazarin followed by dehydrochlorination.

The Friedel-Crafts reaction may be effected either through the reaction of 2-chloromaleic anhydride with hydroquinone or from 2-chlorohydroquinone and maleic anhydride, and an aluminium chloride/sodium chloride melt.

A 2,3-dichloro adduct of naphthazarin may be used in place of the 2-chloronaphthazarin since it loses hydrogen chloride in the heating of the toluene reaction medium. Also, the dimethyl ether or the diacetate of 2-chloronaphthazarin, or 2-bromonaphthazarin can be used with advantage in the reaction. These derivatives may be prepared by methylation or by acetylation by a number of different procedures.

Alternatively, 2-chloronaphthazarin dimethylether may be synthesised by the Diels-Alder reaction of 1,1,4-trimethoxybuta-1,3-diene with 2,6-dichlorobenzo-1,4-quinone.

Naphthazarin itself could be used in the reaction, but it is considerably slower to react, and the working-up is complicated by a number of inseparable impurities.

The invention comprises in another aspect the synthesis of 6-deoxykermesic acid (3,5,8-trihydroxy-1-methyl-9,10-anthraquinone-2-carboxylic acid) by demethylation of the reaction products of methylated cochinellic anhydride with 1,4-dimethoxybenzene by a Friedel-Crafts reaction.

The Friedel-Crafts reaction may be catalysed by BF$_3$ etherate or aluminium chloride/sodium chloride.

The methylated cochinellic anyhydride may be prepared by first reacting a 'bis-TMS-diene' by Diels-Alder addition with a halogenomaleic anhydride (chloro- or bromo-), followed by methylation of the 5-hydroxyl group. Methyl, ethyl and benzyl members of the bis-TMS-diene series may be used. The reaction may be carried out in refluxing toluene solution.

The bis-TMS-diene (alkyl 1-methyl-1,3-bis (trimethylsilyl)-1,3-butadiene-2-carboxylate) may be prepared from an alkyl diacetylacetate by reacting it with trimethylsilyl chloride in the presence of triethylamine in dry solvent. However, other silylating agents include O,N bis-trimethylsilylacetamide and hexamethyldisilazane, the former yielding a mixture of the cis/trans forms, the latter yielding the trans form only.

The invention comprises in another aspect, the synthesis of alkyl 6-deoxykermesate trimethyl ether by methylation of alkyl 6-deoxykermesate in acetone containing K$_2$CO$_3$ and methylating agent.

From this product, an alkyl 3,5,8,9,10-pentamethoxy-1-methylanthracen-2-carboxylate is synthesised by reductive permethylation (Na$_2$SO$_4$/NaOH/Me$_2$SO$_4$/THF) as described the methodology of Kraus and Onman, Synth. Commun., 1986, 16, 1037.

The invention further comprises the C-glucosylation of the above pentamethoxy compound with a glucose derivative.

The glucose derivative may be 2,3,4,6-tetra-O-benzyl D-glucopyranose.

Said glucose derivative is first converted to the 1-trifluoroacetate in situ and C-glucosylation carried out utilising BF$_3$.Et$_2$O as a catalyst to produce the alkyl 7-(2,3,4,6-tetra-O-benzyl-D-glucopyranosyl)-3,5,8,9,10-pentamethoxy-1-methylanthracene-2-carboxylate.

The invention further comprises the production of 6-deoxycarminic acid from the above C-glucosylated compound by the following sequence:

(1) regeneration of the anthraquinone chromophore utilizing Jones reagent at 0° C. or with pyridinium chlorochromate
(2) debenzylation (H$_2$/Pd-C/MeOH-HCl)
(3) saponification (2-5N methanolic NaOH, reflux 6 h) for the methyl and ether esters. For the benzyl compound this step is ommited because the benzyl group is hydrogenolysed simultaneous with the benzyl groups on the glucose group.
(4) acetylation (Ac$_2$O/Pyridine)
(5) regeneration of phenolic groups (BBr$_3$/CH$_2$Cl$_2$/−40° C. −0° C.)

The compound produced is utilized without purification and characterised by acetylation as the hepta-acetate and is hydrolysed in acidic medium (0.5N methanolic HCl/reflux) to give 6-deoxycarminic acid.

The invention further comprises the synthesis of carminic acid by application of the method described from 6-deoxycarminic acid by Dimroth and Kammerer, Chem., Ber. 1920 5313, 471, to the compound produced by step (5) above. Oxidation with lead tetra-acetate and Thiele acetylation produced the octa-acetate compound. Hydroxylsis of the acetate groups (HCl/EtOH/reflux 1 h) gave carminic acid.

The physicochemical identification of the synthetic carminic acid was verified by direct comparison with a sample of the natural product by spectroscopic and elemental analysis.

The synthesis according to the invention will now be described with reference to the following figure and reactions:

FIG. 1 shows the structure of the compounds described in Reactions XI and XII.

FIG. 2 shows the structure of the compounds described in Reactions III and V.

FIG. 3 shows the structure of the compounds described in Reaction VI.

FIG. 3a shows the structure of the compounds described in Reaction VI.

Reaction I—preparation of the bis-trimethylsilyl ether of methyl diacetylacetate.

To a stirred mixture of triethylamine (36.8 g; 0.359 mole) and trimethylchlorosilane (34.2 g; 0.315 mole) in sodium-dried benzene (50 ml), methyl diacetylacetate (10.0 g; 0.0632 mole) in dry benzene were added dropwise over one hour. The reaction mixture was stirred for 24 hours after which gas liquid chromatographic monitoring showed that bis-trimethylsilylation was complete.

Figure 5:
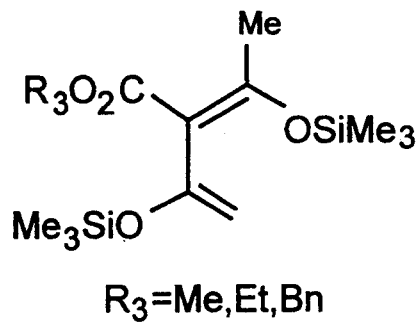
FIG. 5 shows the structure of the compounds described in Reaction I.

The solution was filtered through a short silica gel column equipped with a No. 1 porosity disc. By evaporation of the excess reagents and solvent from the filtrate, a residual orange oil was obtained. Distillation in vacuo gave one fraction, 70°–71° C./0.35 mm Hg, as a faint yellow liquid (18.04 g; 94%) consisting, from NMR examination, of the E and Z isomers of methyl 1-methyl-1,3-bis-trimethylsilyl-buta-1,3-diene-2-carboxylate FIG. 5).

Ethyl and benzyl esters were prepared in similar fashion.

Reaction II—preparation of 2-chloronaphthazarin 2-chloro-5,8-dihydroxy-1,4-naphthoquinone):

A magnetically stirred suspension of commercial naphthazarin (1.00 g) in glacial acetic acid (15 ml) was maintained in contact with a slight excess of chlorine gas for 5 hours, during which time the wine red suspension changed to a bright yellow red. The solution was poured on to ice (about 100 g) to give a suspension which, after allowing the ice to melt, was filtered and the yellow precipitate dried—the dichloro adduct. This (1.36 g) was refluxed in absolute alcohol (50 ml) for 30 mins, whereby solution first occurred followed by HCl elimination.

Figure 4:
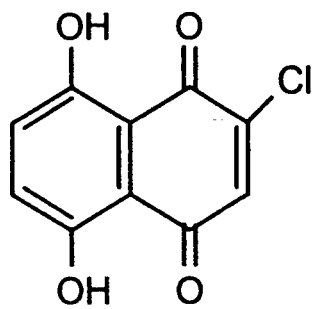
FIG. 4 shows the structure of the compounds described in Reaction II.

2-chloronaphthazarin FIG. 4 crystallised from the viridian coloured solution. The suspension was cooled to 0° C. and the pure product collected as dark red needles with a green metallic sheen (1.004 g; 85%, m.p. 182° C.).

Reaction III—reaction of the bis-TMS-diene and 2-chloronaphthazarin to produce methyl 3,5,8-trihydroxy-1-methyl-9,10-anthroquinone-2-carboxylate:

To a stirred mixture of 2-chloronaphthazarin 1.00 g; 4.45 m mole) in sodium-dried toluene (20 ml), methyl 1-methyl-1,3-bis(trimethylsilyl)-buta-1,3-diene-2-carboxylate (2.00 g; 6.63 m mole) in toluene (5 ml) was added dropwise over a period of two hours and the mixture refluxed for a further 6 hours. After the reaction was cooled to ambient temperature, damp methanol (50 ml) was added and the mixture kept overnight. The solvents were evaporated and the resultant dark brown solid refluxed in chloroform (50 ml) for 30 mins. The mixture was cooled to 60° C. and the orange brown solid collected and dried (0.852 g).

From the filtrate by flash chromatography (eluant, chloroform) further product (0.288 g) was obtained giving a total yield (1.13 g, 78%) of crude product which could be crystallised from nitrobenzene as orange red needles, mp 263°–264° C. The NMR spectrum showed the product to be methyl 6-deoxykermesate. Ethyl 6-deoxykermesate FIG. 2, Compound d, in which $R_3$=Et) (yield 76%, m.p. 230°–231° C.) and benzyl 6-deoxykermesate (FIG. 2, Compound d, in which $R_3$=Bn) (72% yield) were similarly produced.

Reaction IV—preparation of methyl cochinellic anhydride, methyl 3-methyl-5-hydroxyphthalic anhydride-4-carboxylate:

A stirred mixture of commercial 2-bromomaleic anhydride (0.200 g; 1.13 m mole) and the bis-TMS-diene methylester (0.512 g; 1.70 m mole) in dry toluene (5 ml) was refluxed for 24 hours. After the reaction mixture had been cooled to ambient temperature, damp methanol was added to hydrolyse the trimethylsilyl ether. After a further 24 hours, the resultant mixture was allowed to adsorb on to silica gel (3.0 g). Addition of the silica gel to the top of a column of 'flash silica' and elution with chloroform gave a lower band which upon concentration and evaporation gave methyl cochinellic anhydride (0.123 g; 46%) as white needles, m.p. 146° C.).

The ethyl (m.p. 95°–96° C.) and the benzyl derivatives were prepared similarly.

Condensation of the methylated product from the methyl ester with 1,4-dimethoxybenzene in an aluminium chloride/sodium chloride melt gave 6-deoxykermesic acid.

Alkyl 6-deoxykermesates obtained by the above-described procedures can be transformed to a number of different products. Application of the Thiels reaction affords an equal mixture of kermesic and isokermesic acid derivatives.

Reaction V—preparation of methyl 6-deoxykermesate trimethyl ether (methyl 3,5,8-trimethoxy-1-methylanthaquinone-2-carboxylate: Compound (FIG. 2, Compound e/ wherein $R_3$=Me):

A suspension of potassium carbonate (1.00 g), methyl 3,5,8-trihydroxy-1-methylanthraquinone-2-carboxylate (FIG. 2, compound c) (0.300 g, 0.914 mmol) and dimethyl sulphate (0.5 ml) in dry acetone (25 ml) was refluxed for 24 hours. The suspension was allowed to cool to ambient temperature, filtered through a plug of celite, the solids were washed thoroughly with $CH_2Cl_2$, and the filtrate evaporated in vacuo, with excess dimethyl sulphate being removed in high vacuum, Column chromatography (on silica gel using CHCl$_3$ as eluent) of the resultant off-yellow solid gave the corresponding trimethyl ether as a yellow solid (0.288 g, 82%), R$_f$ 0.29 (silica gel/CHCl$_3$), which recrystallised as copious fine yellow needles from ethylacetate, m.p. 249°-250° C.

Preparation of benzyl 6-deoxykermesate trimethyl ether (benzyl 3,5,8 trimethoxy-1-methylanthra-9,10-quinone-2-carboxylate Compound (FIG. 2, Compound c, wherein R$_3$=Bn):

A suspension of benzyl 3,5,8-trihydroxy-1-methylanthra-9,10-quinone-2-carboxylate (8.00 g, 0.02 mol), anhydrous potassium carbonate (30.0 g, 0.22 mol) and dimethylsulphate (15 ml, 20.0 g, 0.13 mol) in dry acetone (100 ml) was refluxed for 24 h with exclusion of moisture. The solvent was removed in vacuo, cold water (200 ml) added and after 0.5 h the suspension exhaustively extracted with dichloromethane. The combined extracts were dried (anhydrous Na$_2$SO$_4$), filtered and evaporated in vacuo to give a brown viscous oil (8.12 g, 92%) which crystallised from absolute ethanol as orange needles, m.p. 211°-212° C.

Reaction VI—preparation of methyl 3,5,8,9,10-pentamethoxy-1-methylanthracene-2-carboxylate (FIG. 3, wherein R$_3$=Me); reference: G A Kraus and T O Man, Synth. Commun., 1986, 16 (9), 1037:

To a vigorously stirred suspension of methyl 3,5,8-trimethoxy-1-methylanthraquinone-2-carboxylate (0.271 g, 0.732 mmol) in THF (2 mls) containing tetra n-butylammonium bromide (0.030 g, 0.093 mmol) under nitrogen, was added aqueous sodium dithionite (0.9 g, dissolved in the minimum amount of distilled water). After 15 minutes at ambient temperature aqueous potassium hydroxide (0.94 g, 16.8 mmol, dissolved in the minimum amount of water) was added, After further 10 minutes, dimethyl sulphate (1.50 mls, 15.8 mmol) was added and the system vigorously stirred overnight (15 hours). The product was isolated by partitioning between water and CH$_2$Cl$_2$. The organic layer was separated, dried (Na$_2$SO$_4$), filtered, evaporated in vacuo and purified by silica gel chromatography, by eluting quickly with CHCl$_3$ whilst shielding the column and the collected fractions from direct light. This gave a yellow viscous syrup (0.220 g, 75%), R$_f$ 0.45 (CHCl$_3$) which failed to crystallise.

Preparation of benzyl 3,5,8,9,10-pentamethoxymethanthracene-2-carboylate (FIG. 3, wherein R$_3$=Bn):

To a finely divided suspension under nitrogen of benzyl 3,5,8-trimethoxy-1-methylanthra-9-10-quinone-2-carboxylate (2.00 g, 4.48 mmol) and tetrabutylammonium bromide (0.168 g) in THF (20 ml) was added aq. sodium dithionite (5.50 g dissolved in the minimum amount of water). The system was stirred for 15 min, aq. potassium hydroxide (5.78 g dissolved in the minimum amount of water) was added and the system stirred for a further 10 min, then cooled to 0° C. and dimethylsulphate (9.0 ml) slowly dripped in. The mixture was kept at 0° C. for 30 min, then allowed to warm to ambient temperature and stirred overnight. Dichloromethane (100 ml) was added and the organic layer washed twice with water (100 ml) portions), dried (anhydrous Na$_2$SO$_4$), filtered and evaporated in vacuo to give a brown viscous oil (2.01 g 94%) which crystallised from ether/petrol as a light green-yellow luminous solid, m.p. 135°-137° C.

In addition to the protective group methyl in the penta-methoxy intermediate (FIG. 3), other general protective groups (R) may be used including CAc and OSiMe$_3$ (FIG. 3a).

Figure 6:
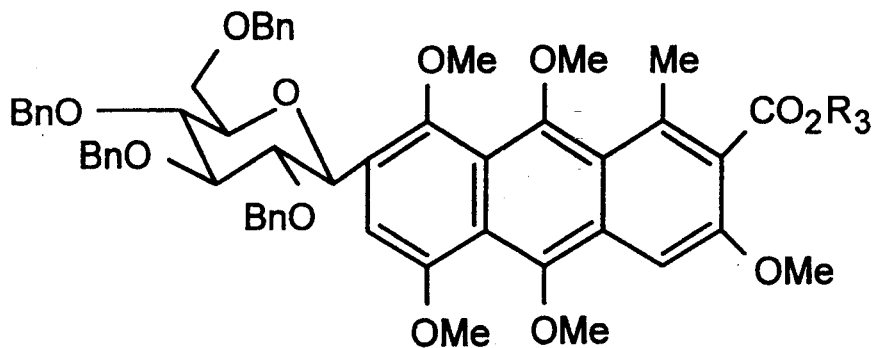
FIG. 6 shows the structure of the compounds described in Reactions VII and VIII.
Figure 7:
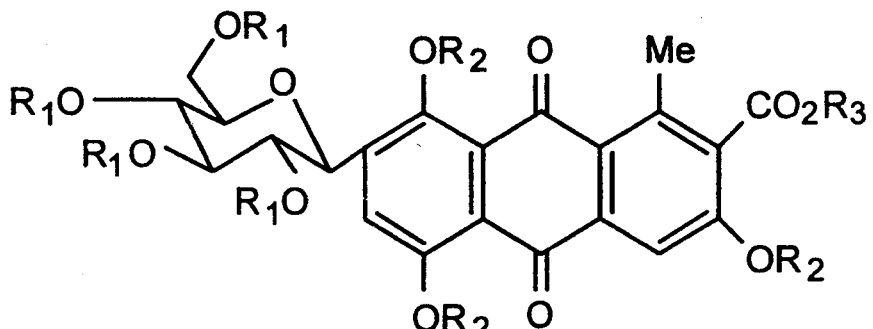
FIG. 7 shows the structure of the compounds described in Reactions VIII, IX, X, XII.

Reaction VII—C-Glycosylation of methyl 3,5,8,9,10-pentamethoxy-1-methylanthracene-2-carboxylate with 1-trifluoroacetyl-2,3,4,6-tetra-O-benzyl-D-glucopyranose (FIG. 6, wherein R$_3$=Ne), and Reaction VIII Regeneration of the anthraquinone chromophore methyl 7-β-D-2,3,4,6-tetra-0-benzylguco-pyranosyl-1-methyl-3,5,8-trimethoxyanthra-9,10, quinone-2-carboxylate (FIG. 7, compound a)

To a stirred solution of 2,3,4,6-tetra-O-benzyl-D-glucopyranose (0.100 g, 0.185 mmol) and methyl 3,5,8,9,10-pentamethoxy-1-methyl-anthracene-2-carboxylate (0.220 g, 0.55 mmol) in dry CH$_2$Cl$_2$ (4 ml) at ambient temperature under nitrogen and shielded from light was added trifluoroacetic anhydride (0.200 ml, 0.297 g, 1.41 mmol). After 3 hours, boron trifluoride etherate (0.050 ml, 0.058 g, 0.407 mmol) was added. The mixture was stirred at ambient temperature for 2.5 hours, 10% aqueous HCl (20 ml) added and the mixture extracted once with CH$_2$Cl$_2$. The organic layer was evaporated in vacuo to give a crude product which was dissolved in acetone, cooled to 0° C. and treated carefully with micro-drops of Jones' reagent until t.l.c. (silica gel/CHCH$_3$) indicated an absence of the pentamethoxyanthracene derivative. The resultant mixture was dissolved in distilled water (50 ml) and extracted once with CH$_2$Cl$_2$. The organic layer was dried (Na$_2$SO$_4$), filtered, evaporated in vacuo and the crude product separated by prep. t.l.c. on silica gel using ether:hexanes (7:3) as eluent to give two products, methyl 3,5,8-trimethoxy-1-methylanthraquinone-2-carboxylate (0.122, 60%) and the corresponding quinone C-glycoside as a yellow syrup (0.036 g, 21%) R$_f$ 0.32 (silica gel/ether:-hexanes (7:3)). 3-Glucosylation of benzyl 3,5,8,9,10-pentamethoxy-1-methylanthracene-2-carboxylate with 1-trifluoroacetyl-2,3,4,6-tetra-O-benzyl-D-glucopyranose (FIG. 6, wherein R$_3$=Bn) of FIG. 1); and Regeneration of the anthraquinone chromophore benzyl-7-β-(2,3,4,6-tetra-O-benzyl-D-glucopyranosyl) 3,5,8-trimethoxy-1-methylanthra-9,10-guinone-2-carboxylate (FIG. 7, compound g)

To a stirred suspension under dry nitrogen of 2,3,4,6-tetra-O-benzyl-D-glucopyranose (1.00 g, 1.85 mmol) in dry dichloroethane (10 ml) was added fresh trifluoroacetic anhydride (1 ml); a solution soon formed which was stirred for 4 h at ambient temperature. Evaporation of the solvent in vacuo at ambient temperature gave a clear viscous syrup to which was added benzyl 3,5,8,9,10-pentamethoxy-1-methylanthracene-2-carboxylate (1.76 g 3.70 mmol) and dry dichloromethane 5 ml) and the system kept under dry nitrogen. The stirred solution was shielded from light, cooled to −40° C. (acetonitrile/CO$_2$) and cold (−40° C.) boron trifluoride-etherate (0.25 ml) added dropwise. The mixture was kept at −40° C. for 1 h, then allowed to return to ambient temperature and stirred overnight. 1.0M HCl (aq.) (7.5 ml) was added and the mixture partitioned between water and dichloromethane. The organic layer was dried (anhydrous Na$_2$SO$_4$), filtered, evaporated in vacuo; the residue dissolved in dry dichloromethane, pyridinium chlorochromate (0.8 g) added and the suspension stirred for 15 min. Dry ether (200 ml) was added and stirring continued for a further 15 min. The vacuo and the product purified by flash chromotography on silica gel using gradient elusion with ether/petrol. A brown viscous impure syrup (1.78 g) was obtained, $R_f$ 0.38 (silica gel/ether:petrol (50:50)) which was directly debenzylated.

Reaction IX—production of 6-deoxycarminic acid:

Preparation of methyl 7-$\beta$-D-glucopyranosyl-1-methyl-3,5,8-trimethoxy anthra-9,10-quinone-2-carboxylate by hydrogenolysis of the benzyl protecting groups, (FIG. 7, Compound b)

To a stirred solution of the per-O-benzylglycoside (0.020 g, 0.022 mmol) in THF (5 ml) at ambient temperature was added 10% Pd/C (5 mg) and a micro-drop of conc. HCl. The reaction vessel was evacuated by using standard aspirator suction and the vacuum relieved by introduction of $M_2$ Gas. This evacuation/$M_2$ flushing sequence was repeated 4 times, and the mixture was allowed to stir vigorously for 24 hours. The green-yellow suspension was filtered through a plug of celite, evaporated in vacuo, dissolved in abs. ethanol (10 ml) and allowed to stand exposed to the air for 24 hours thus restoring the quinone centre which had been reduced. The product was purified by prep. t.l.c. on silica gel using CHCl$_3$:ethanol (2:1) as eluent to give a yellow solid (5.0 mg, 41%), $R_f$ 0.45 (silica gel/CHCl$_3$:ethanol (2:1)).

Preparation of 7-$\beta$-D-glucopyranosyl-3,5,8-trimethoxy-1-methylanthra-9,10-quinone-2-carboxylic acid (FIG. 7, Compound b, wherein R$_3$=H) by hydrogenolysis of benzyl protecting groups:

To a stirred solution of the per-O-benzyl C-glycoside (0.01M) in THF containing 1 drop of conc. HCl per 10 ml of solvent was added 10% Pd/C (0.1 equiv.). The reaction vessel was evacuated by using standard aspirator suction and the vacuum relieved by introduction of H$_2$ gas. This evacuation/H$_2$ flushing sequence was repeated 4 times, and the mixture was allowed to stir vigorously for 24 hrs at ambient temperature. The green-yellow suspension was filtered through a lug of celite evaporated in vacuo, dissolved in THF and allowed to stand in the dark, exposed to the air for 24 hrs thus restoring the quinone centre which had been reduced. The product was purified by chromatography on silica gel using gradient elution with CHCl$_3$:ethanol. In this way the crude benzyl 7-$\beta$-(2,3,4,6-tetra-Obenzyl-D-glucopyranosyl)-3,5,8-trimethoxy-1-methylanthra-9,10-quinone-2-carboxylate (1.78 g) obtained by glycosylation and regeneration of the quinone system was treated as above and gave after flash chromatography, a light yellow glass (0.627 g, 65%), $R_f$ 0.64 (silica gel/CHCl$_3$-methanol (1:1), which was directly acetylated.

Saponification was required for the methyl and ethanol compounds of the series, but for the benzyl compounds the 2-carboxylic acid was produced as described simultaneously during the hydrogenolysis of the O-benzyl group on the glucose component. The subsequent steps in this series of acetylation, demethylation and characterisation of the product are described, namely, Reactions X, XI and the acetylation of the product from Xi to give 6-deoxy carminic acid heptaacetate.

Reaction X—Acetylation of 7-$\beta$-D-glucopyranosyl)-3,5,8-trimethoxy-1-methyl-anthra-9,10-quinone-2-carboxylic acid (FIG. 7, Compound b, wherein R$_3$=H) to give the compound shown in FIG. 7, Compound d To a stirred suspension of 7-$\beta$-D-glucopyranosyl-3,5,8-trimethoxy-1-methyl-anthra-9,10-quinone-2-carboxylic acid (0.627 g, 1.21 mmol) in dry dichloromethane (60 ml) was added pyridine. (3.85 ml, 48.3 mmol), acetic anhydride (2.0 ml, 0.021 mmol) and dimethylaminopyridine (0.014 g). The mixture was stirred for 72 h, washed with 0.1M aq. HCl (600 ml), dried (anhydrous Na$_2$SO$_4$), filtered, evaporated in vacuo and products separated by flash chromatography on silica gel using gradient elution with chloroform:petrol to give the following:

7-$\beta$-(2,3,4,6-tetra-O-acetyl-D-glucopyranosyl)-3,5,8-trimethoxy-1-methylanthra-9,10-quinone-2-carboxylic acid (FIG. 7, Compound d); 0.34 g (41%), $R_f$0.45 (silica gel/CHCl$_3$:methanol (4:1)), partially acetylated material 0.195 g, and an impurity (0.236 g) (30%) $R_f$ 0.61, (silica gel/CHCl$_3$:ethylacetate (1:1)).

Reaction XI—regeneration of phenolic groups by demethlation of compound (7d) to produce 7-$\beta$-(2,3,4,6-tetra-O-acetyl-D-glucopyranosyl)-3,5,8-trihydroxy-1-methylanthra-9,10-quinone-2-carboxylic acid (FIG. 7, Compound c)

To a stirred solution of 7-$\beta$-(2,3,4,6-tetra-O-acetyl-D-glucopyranosyl)-3,5,8-trimethoxy-1-methylanthra-9,10-quinone-2-carboxylic acid (250 mg, 0.36 mmol) in dry dichloromethane (33 ml) at $-40°$ C. was added dropwise a cold solution of 0.1M boron tribromide in dichloromethane (3.7 ml). The temperature of the solution was slowly allowed to rise to 0° C. and maintained at this temperature for 24 h. Dilute aq. HCl (0.1 m) (30 ml) was added to the mixture which was vigorously stirred for 10 min. The aqueous solution was exhaustively extracted with dichloromethane, the extracts were combined, dried (Na$_2$SO$_4$), filtered, and evaporated in vacuo to give a dark orange glass, 0.157 g (67%), $R_f$0.35 (silica gel/chloroform:methanol (5:1)). Acetylation of this gave the heptaacetate (Compound (1d); R$_1$=H, R$_2$=Ac) which provided identical to deoxycarminic acid heptaacetate (FIG. 1, Compound d, wherein; R$_3$=H, R$_2$=Ac) prepared from natural carminic acid.

Reaction XII—production of carminic acid octa acetate, (7-$\beta$-(2,3,4,6-tetra-O-acetyl-D-glucopyranosyl)-3,5,6,8-tetraacetoxy-1-methylanthra-9,10-quinone-2-carboxylic acid. (FIG. 1, Compound c)

To a solution of 7-$\beta$-(2,3,4,6-tetra-O-acetyl-D-glucopyranosyl)-3,5,8-trihydroxy-1-methylanthra-9,10-quinone-2-carboxylic acid (FIG. 7, Compound c) (54 mg, 0.084 mmol) in acetic anhydride (3 ml) was added lead tetraacetate (100 mg) and the suspension stirred for 9 h, after the red solution had turned green-orange. Acetic anhydride (1 ml) containing 5 drops of conc. sulphuric acid was introduced, white lead salts soon formed and the solution turned orange. Stirring was continued overnight, dichloromethane was added, the solution was filtered through celite and washed with 5% aq. solution chloride. The organic layer was dried (anhydrous Na$_2$SO$_4$), filtered and evaporated in vacuo to give an orange residue, 57 mg, (82%) which was crystallised from abs. ethanol.

Synthesis of carminic acid (FIG. 1, Compound a)

Hydrolysis of the acetate groups of synthetic carminic acid octaacetate by known methods with ethanolic hydrochloric acid produced carminic acid, which was identical to natural carminic acid.

It is claimed:

1. A method of synthesis of R' 6-deoxykermesates comprising reacting a 2-halogeno-5,8-dihydroxy-1,4-naphthoquinone with a R' 1-methyl-1,3-bis-(trimethylsilyl)-1,3-butadiene-2-carboxylate, wherein R' is one of an alkyl and benzyl.

2. A method according to claim 1, wherein the 2-halogeno-5,8-dihydroxy-1,4-naphthoquinone is 2-halogeno-5,8-dihydroxy-1,4-naphthoquinone dimethyl ether.

3. A method of according to claim 1, wherein the 2-halogeno-5,8-dihydroxy-1,4-naphthoquinone is 2-halogeno-5,8-dihydroxy-1,4-naphthoquinone diacetate.

4. A method according to claim 1, wherein the 2-halogeno-5,8-dihydroxy-1,4-naphthoquinone is 2-chloro-5,8-dihydroxy-1,4-naphthoquinone.

5. A method according to claim 1, wherein the 2-halogeno-5,8-dihydroxy-1,4-naphthoquinone is 2-bromo-5,8-dihydroxy-1,4-naphthoquinone.

6. A method according to claim 4, wherein chlorine is added to 5,8-dihydroxy-1,4-naphthaquinone to give the adduct 2,3-dichloro-5,8-dihydroxy-1,4-naphthaquinone followed by dehydrochlorination to give 2-chloro-5,8-dihydroxy-1,4-naphthaquinone.

7. A method according to claim 4, wherein the Friedel-Crafts reaction is used to synthesize 2-chloro-5,8-dihydroxy-1,4-naphthaquinone from 2-chloromaleic anhydride with hydroquinone.

8. A method according to claim 4, wherein the Friedel-Crafts reaction is used to synthesize 2-chloro-5,8-dihydroxy-1,4-naphthaquinone from 2-chlorohydroquinone, maleic anhydride, and a melt of a mixture of aluminium chloride and sodium chloride.

9. A method according to claim 2, wherein 2-chloro-5,8-dihydroxy-1,4-naphthaquinone dimethylether is synthesize by the Diels-Alder reaction of 1,1,4-trimethoxybuta-1,3-diene with 2,6-dichlorobenzo-1,4-quinone.

10. A method of synthesis of 5-methoxy cochinellic anhydride, comprising the steps of first reacting a R' 1-methyl-1,3-bis(trimethylsilyl)-1,3-butadiene-2-carboxylate by Diels-Alder addition with either chloromaleic anhydride or bromomaleic anhydride followed by methylation of the 5-hydroxyl group, wherein R' is one of an alkyl and a benzyl.

11. A method according to claim 10, wherein R' is one of methyl, ethyl and benzyl.

12. A method according to claim 10, wherein the reaction is carried out in refluxing toluene.

13. A method according to claim 10, wherein the R' 1-methyl-1,3-bis (trimethylsilyl)-1,3-butadiene-2-carboxylate is prepared by reacting R' diacetylacetate with a silylating agent in the presence of triethylamine in dry solvent.

14. A method according to claim 13, wherein trimethylsilyl chloride is used as the silylating agent.

15. A method according to claim 13, wherein O,N bis-trimethylsilylacetamide is used as the silylating agent.

16. A method according to claim 13, wherein hexamethyldisilazane is used as the silylating agent.

17. A method of producing a C-glucosylated compound, comprising the step of C-glucosylation of a R' 3,5,8,9,10-pentamethoxy-1-methylanthracen-2-carboxylate with a 1-trifluoroacetate glucose derivative to give the 7-glucosyl derivative of a R' 3,5,8,9,10-pentamethoxy-1-methylanthracen-2-carboxylate, wherein said glucose derivative is first converted to the 1-trifluoroacetate in situ and C-glucolysation is carried out using the boron trifluoride etherate as a catalyst.

18. A method of producing a C-glucosylated compound according to claim 17, wherein the glucose derivative is 1-trifluoroacetyl-2,3,4,6-tetra-O-benzyl-D-glucopyranose.

19. A method of producing 6-deoxycarminic acid from a C-glucosylated compound produced according to the method of claim 17, wherein the C-gluocosylated compound is produced by synthesizing a R' 6-deoxykermesate trimethyl ether by methylation of a R' 6-deoxykermesate in acetone containing potassium carbonate and methylating agent, with a glucose derivative 1-trifluoroacetyl-2,3,4,6-tetra-O-benzyl-D-glucopyranose to give the 7-glucosyl derivative of a R' 2,3,8,9,10-pentamethoxy-1-methyl anthracen-2-carboxylate, said glucose derivative being converted to the 1-trifluoroacetate in situ, synthesizing a R' 3,5,8,9,10-penta-methoxy-1-methylanthracen-2-carboxylate by reductive permethylation of the R' 6-deoxykermesate trimethyl ether, and C-glucosylation of a R' 3,5,8,9,10-penta-methoxy-1-methylanthracen-2-carboxylate being carried out utilizing boron trifluoride etherate as a catalyst to produce the R' 7-(2,3,4,6-tetra-O-benzyl-D-glucopyranosyl)-3,5,8,9,10-pentamethoxy-1-methylanthracene-2-carboxylate starting material, where R' is benzyl, comprising the steps of, in sequence:
(1) regeneration of the anthraquinone chromophore utilizing one of Jones reagent at 0° C. and pyridinium chlorochromate
(2) debenzylation
(3) acetylation
(4) regeneration of phenolic groups, and
(5) acetylation to produce the hepta-acetate which is hydrolyze in acidic medium to give 6-deoxycarminic acid.

20. A method of synthesis of carminic acid from 6-deoxycarminic acid produced by claim 19 consisting of oxidation of 6-deoxycarminic acid with lead tetraacetate and Thiele acetylation with a mixture of acetic anhydride and concentrated sulphuric acid to produce the octa-acetate compound, followed by hydrolysis of the acetate groups by refluxing for one hour with a mixture of ethanol and hydrochloric acid.

21. A method of producing 6-deoxycarminic acid from a C-glucosylated compound produced according to the method of claim 17, wherein the C-gluocosylated compound is produced by synthesizing a R' 6-deoxykermesate trimethyl ether by methylation of a R' 6-deoxykermesate in acetone containing potassium carbonate and methylating agent, with a glucose derivative 1-trifluoroacetyl-2,3,4,6-tetra-O-benzyl-D-glucopyranose to give the 7-glucosyl derivative of a R' 3,5,8,9,10-pentamethoxy-1-methyl anthracen-2-carboxylate, said glucose derivative being converted to the 1-trifluoroacetate in situ, synthesizing a R' 3,5,8,9,10-penta-methoxy-1-methylanthracen-2-carboxylate by reductive permethylation of the R' 6-deoxykermesate trimethyl ether, and C-glucosylation of a R' 3,5,8,9,10-penta-methoxy-1-methylanthracen-2-carboxylate being carried out utilizing boron trifluoride etherate as a catalyst to produce the R' 7-(2,3,4,6-tetra-O-benzyl-D-glucopyranosyl)-3,5,8,9,10-pentamethoxy-1-methylanthracene-2-carboxylate starting material, where R' is one of methyl and ethyl, comprising the steps of, in sequence:

(1) regeneration of the anthraquinone chromophore utilizing one of Jones reagent at 0° C. and pyridinium chlorochromate
(2) debenzylation
(3) saponification
(4) acetylation
(5) regeneration of phenolic groups to produce 7-β-(2,3,4,6-tetra-O-acetyl-D-glyucopyranasyl)-3,5,8-trihydroxy-1-methylanthra-9,10-quinone-2-carboxylic acid, and
(6) acetylation to produce the hepta-acetate which is hydrolyzed in acidic medium to give 6-deoxycarminic acid.

22. A method of synthesis of carminic acid from 6-deoxycarminic acid produced by claim 21 consisting of oxidation of 6-deoxycarminic acid with lead tetraacetate and Thiele acetylation with a mixture of acetic anhydride and concentrated sulphuric acid to produce the octa-acetate compound, followed by hydrolysis of the acetate groups by refluxing for one hour with a mixture of ethanol and hydrochloric acid.

23. A method of producing a C-glucosylated compound according to claim 17, wherein the R' 3,5,8,9,10-pentamethoxy-1-methylanthracen-2-carboxylate is synthesized by reductive permethylation of a R' 6-deoxykermesate trimethyl ether.

24. A method of producing a C-glucosylated compound according to claim 23, wherein the R' 6-deoxykermesate trimethylether is synthesized by methylation of a R' 6-deoxykermesate in acetone containing potassium carbonate and a methylating agent.

25. A method of producing a C-glucosylated compound according to claim 24, wherein the R' 6-deoxykermesate is formed from a 3,5,8-trihydroxy-1-methyl-9,10-anthraquinone-2-carboxylic acid starting material.

26. A method of producing a C-glucosylated compound according to claim 25, wherein 6-deoxykermesic acid is synthesized by the demethylation of methyl 3,5,8-trimethoxy-1-methyl-9,10-anthraquinone-2-carboxylate produced by a Friedel-Crafts reaction of 5-methoxycochinellic anhydride with 1,4-demethoxybenzene.

27. A method 26, wherein the Friedel-Crafts reaction is catalyzed by boron trifluoride etherate.

28. A method according to claim 26, wherein the Friedel-Crafts reaction is catalyzed by a melt of a mixture of aluminium chloride and sodium chloride.

* * * * *